United States Patent
Ormerod et al.

(10) Patent No.: US 6,958,153 B1
(45) Date of Patent: Oct. 25, 2005

(54) SKIN PENETRATION ENHANCING COMPONENTS

(75) Inventors: Anthony David Ormerod, Aberdeen (GB); Arthur Winfield, Kuwait University (KW)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/530,375

(22) PCT Filed: Nov. 5, 1998

(86) PCT No.: PCT/GB98/03317

§ 371 (c)(1),
(2), (4) Date: Jul. 7, 2000

(87) PCT Pub. No.: WO99/24036

PCT Pub. Date: May 20, 1999

(30) Foreign Application Priority Data

Nov. 7, 1997 (GB) .............................. 9723669

(51) Int. Cl.$^7$ ................................................. A61K 9/00
(52) U.S. Cl. ..................... 424/400; 514/946; 514/859; 514/861; 514/863
(58) Field of Search .......................... 424/401; 514/946

(56) References Cited

U.S. PATENT DOCUMENTS

| | | | |
|---|---|---|---|
| 4,335,115 A | 6/1982 | Thompson et al. | 424/181 |
| 5,376,646 A * | 12/1994 | Pittrof et al. | 514/78 |
| 5,648,389 A * | 7/1997 | Gans et al. | 514/557 |
| 2001/0031769 A1 * | 10/2001 | Jackman et al. | 514/340 |

FOREIGN PATENT DOCUMENTS

| | | | |
|---|---|---|---|
| DE | WO 96/13249 | * | 5/1996 |
| EP | 0 027 286 A | | 4/1981 |
| EP | 0 043 738 A | | 1/1982 |
| EP | 0 273 202 A | | 7/1988 |
| EP | 0 435 436 A2 | * | 7/1991 |
| EP | 0 435 436 A | | 7/1991 |
| EP | 0 474 126 A | | 3/1992 |
| EP | 0 582 239 A | | 2/1994 |
| EP | 0 753 297 A | | 1/1997 |
| JP | 8-133979 | | 5/1996 |
| WO | 44 18 115 A | | 12/1994 |
| WO | WO 96/13249 | * | 5/1996 |
| WO | WO 96 13249 A | | 5/1996 |

* cited by examiner

Primary Examiner—Shelley A. Dodson
Assistant Examiner—Konata M. George
(74) Attorney, Agent, or Firm—Finnegan, Henderson, Farabow, Garrett & Dunner, L.L.P.

(57) ABSTRACT

The present invention relates to a topical formulation for the treatment of a dermatological condition which comprises a macrocyclic lactone antibiotic, immunosuppresive macrolide or a biologically active analogue, derivative or pro-drug thereof; characterized in that it further comprises a permeation modulator and the permeation modulator and the macrocyclic lactone or macrolide or the biologically active analogue, derivative or pro-drug thereof are present in relative amounts such that when a therapeutic amount is applied to the skin a minimal systemic effect is produced. The immunosuppressive macrolide may be sirolimus.

28 Claims, 3 Drawing Sheets

SKIN PENETRATION ENHANCING COMPONENTS

Figure 1:
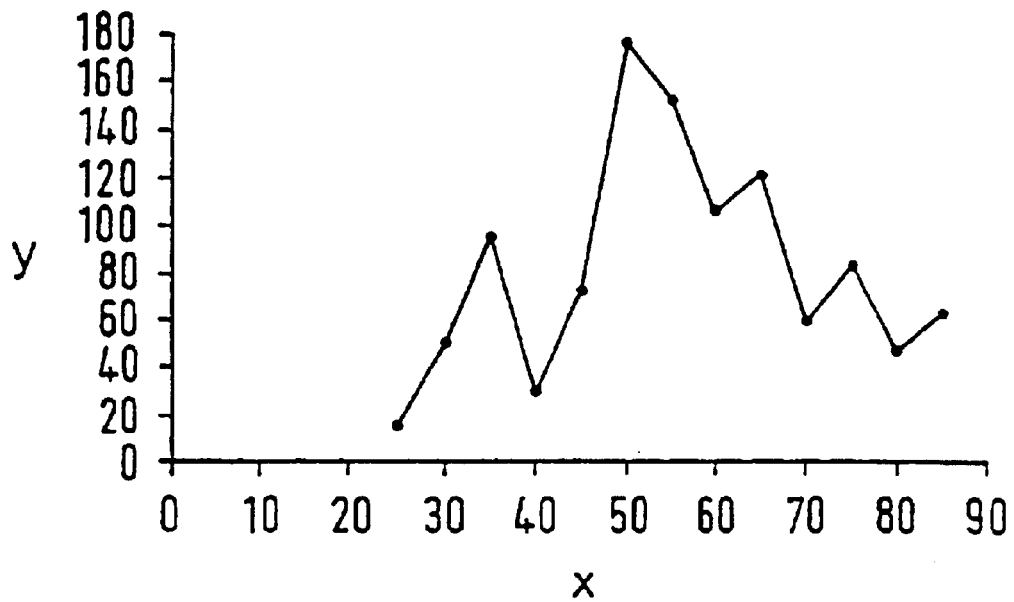
Figure 2:
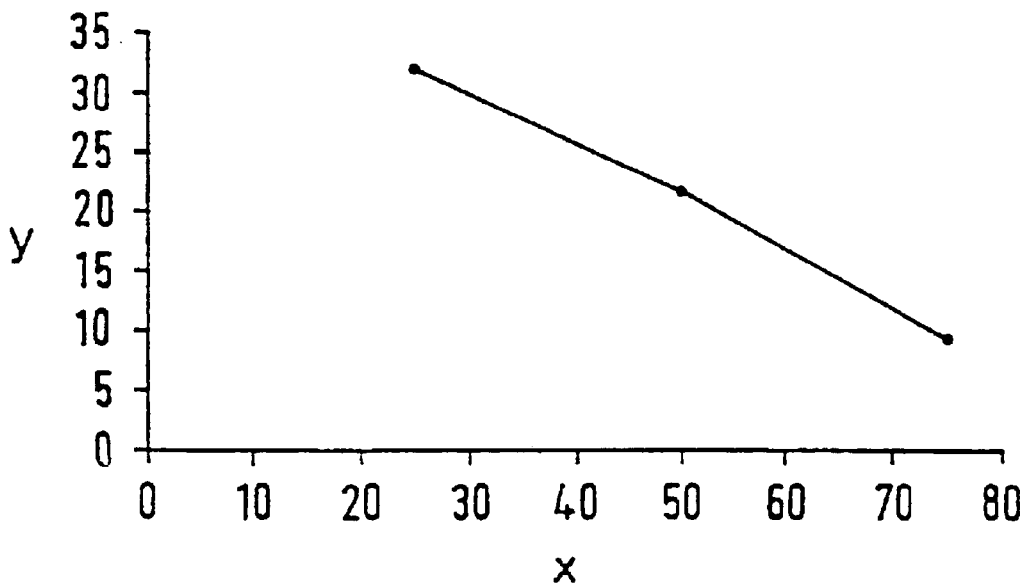
Figure 3:
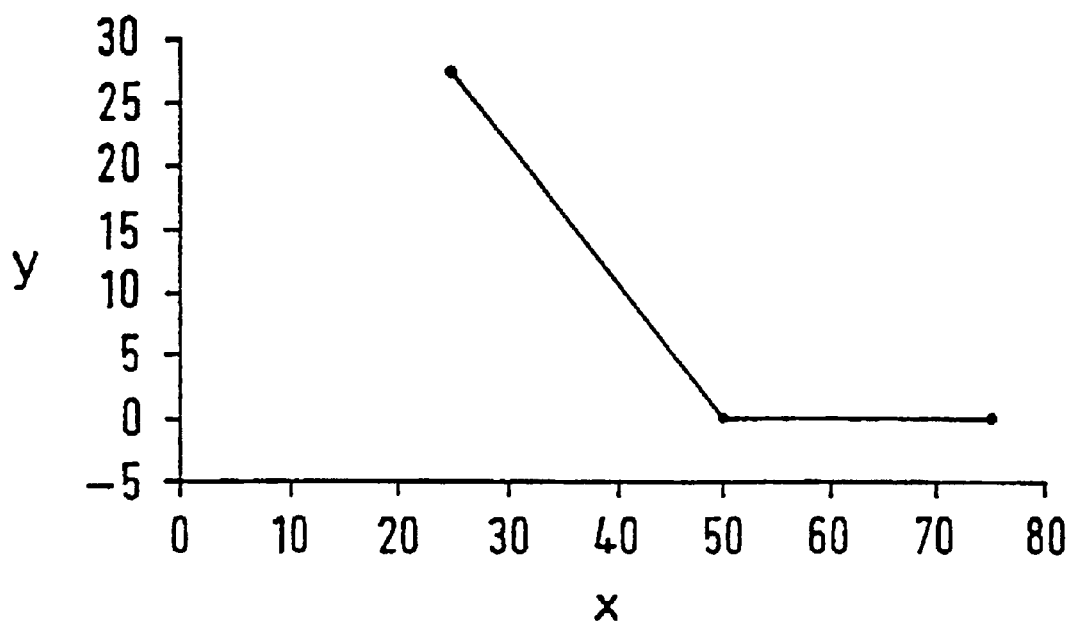
Figure 4:
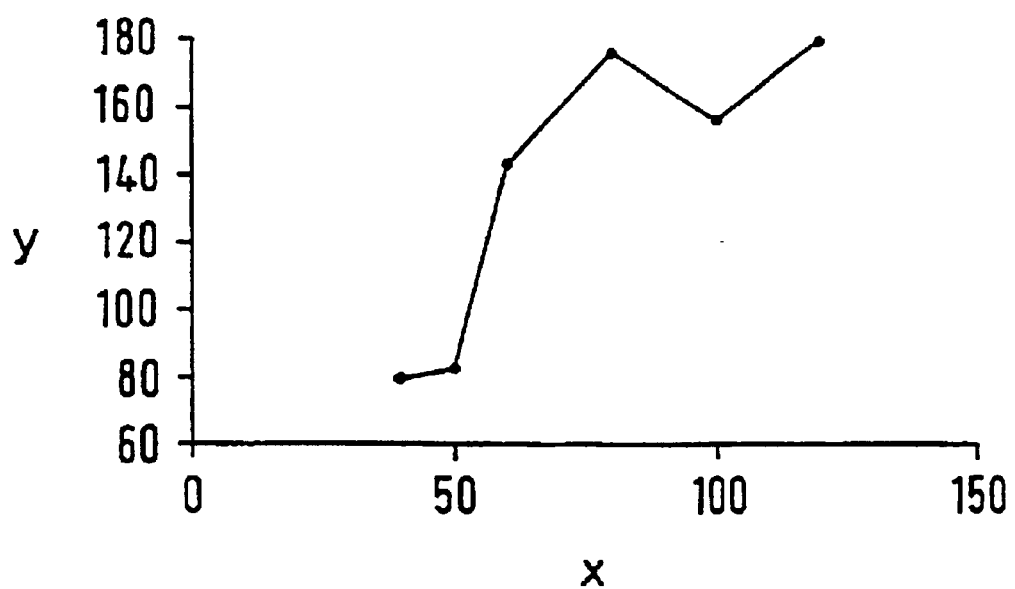

This present invention relates to an effective treatment for psoriasis and other dermatological conditions using a topically applied immunosuppressive agent. The preferred formulation does not allow the agent to appear in the blood or other circulatory system at any significant level.

Dermatological conditions can be uncomfortable and embarrassing for the patient, so an effective safe treatment is required. Some dermatological conditions are caused by an overactive immune system, examples are psoriasis, alopecia, lichen planus, lupus erythematosus, pyoderma gangrenosum, vitiligo and graft versus host disease. Others can be due to bacterial or pustular skin infections.

Dermatological conditions caused by an overactive immune system can be treated by immunosuppressive macrolides, for example sirolimus (rapamycin), FK-506 (tacrolimus) or SDZ ASM 981. Those that are caused by bacteria or are deeper skin infections, such as acne vulgaris and hidranitis suppcurativa, can be treated by macrolide antibiotics, for example erythromycin, azithromycin and clarithromycin. The above agents may be applied by means of topical creams and lotions or taken orally.

Psoriasis affects 2.4% of the population and the current understanding of the pathogenesis of the disease is that it is driven initially by immunocytes. These and keratinocytes are mutually stimulated and activated through the production of cytokines, TGFa, IL-6 and IL-8 from lymphocytes. This leads to a hyperproliferative epidermis with rapid 36 hour cycling of the transient amplifying compartment of keratinocytes.

FK506 is a macrolide antibiotic which shows part homology with sirolimus. Research in models has shown that it has some efficacy in the topical therapy of contact dermatitis, atopic eczema and to a lesser degree psoriasis. Cyclosporin is also known to be effective in treating a wide range of skin diseases. However the usefulness of these drugs is limited by their potential side effects resulting from systemic administration.

Other forms of treatment of dermatological conditions may include using topical steroids but these have undesirable effects such as irreversible atrophy and purpura.

In the treatment of the human or animal body, one of the considerations is that any medicament shall as far as possible affect only the afflicted part. It is well known that amounts of circulating drug should be kept as low as possible to avoid unwanted mutations. A problem with the topical application of medicaments to the skin for example, is that the medicament tends to penetrate the skin and establish itself in the circulating blood system. This is not what is intended in the treatment of dermatological conditions.

The macrocyclic lactone antibiotic rapamycin for example as disclosed in EP-A-0533433 has already been used topically to treat such skin disorders as psoriasis and dermatitis. However no attempt has been made to reduce the amount of rapamycin translocated across the skin into the systemic system. Nor is there any discussion of the reduction of the levels of circulating rapamycin or other macrolide drug at the same time as providing therapeutically effective treatment for a variety of skin disorders.

We have now found that this may be achieved by the addition to such drugs of a permeation modulator. Permeation enhancers are well known as a class of drug translocation facilitors, but the purpose of these is to increase the drug flux across the skin. A permeation modulator however has the facility to allow the drug to penetrate the skin, and particularly the stratum corneum, without significantly passing through the epidermis into systemic systems (eg the blood or lymph systems).

It is also known that immunosuppressive agents taken orally and steroids applied topically can be used to treat dermatological conditions, such as psoriasis or eczema. However, they are often non-specific in their action which leads to undesirable side effects. Thus it would be desirable to develop a topical delivery formulation for an immunosuppressive agent which preferentially treats the diseased sites only and avoids significant systemic exposure; so reducing harmful side effects.

Sirolimus is a macrocyclic lactone antibiotic produced by the organism *Streptomyces hygroscopicus*; it is known to have potent immunosuppressive activities. Sirolimus acts through specific binding of a family of cytosolic immunophilins called the FK binding proteins (FKBP). The sirolimus FKBP complex acts at least three sites. Firstly, by blocking the phosphorylation activation of p70 s6 kinase, an enzyme acting on the 40S ribosomal subunit s6 protein, thereby reducing the efficiency of translation. Secondly by preventing activation of specific elongation factors required for protein synthesis. Thirdly, it inhibits enzyme activity of the cyclin dependent kinase cdk-cyclin E complex which forms one of the tight controls of the G1/S transition in cell division by inhibiting the normal decline of the p27 cdk inhibitor which would follow IL-2 stimulation. Sirolimus has an advantage over other immunosuppressive agents in the treatment of psoriasis as it has an inhibitory effect on keratinocyte proliferation. In vitro experiments have shown that this inhibitory effect takes place at concentrations ranging from 3–10 $\mu$g/ml. A broader range may be employed for example 1 to 20 $\mu$g/ml, but the more efficacious range is 5–8 $\mu$g/ml.

According to the first aspect of the invention, there is provided a topical formulation for the treatment of a dermatological condition which comprises a macrocyclic lactone antibiotic or immunosuppressive macrolide or a pharmacologically active analogue, derivative or pro-drug thereof; characterised in that it further comprises a permeation modulator and the permeation modulator and the macrocyclic lactone antibiotic, immunosuppressive macrolide or pharmacologically active analogue, derivative or pro-drug are present in relative amounts such that when a therapeutic amount is applied to the skin, a minimal systemic effect is produced.

By the term "minimal systemic effect", is meant that the amount of active principal detectable in the blood stream is preferably less than 0.3 ng/nl over 4 to 24 hours after administration, more preferably below 0.1 ng/ml over the same period.

Preferably the macrocyclic lactone antibiotic is selected from erythromycin, azithromycin or clarithromycin. These macrocyclic lactone antibiotics are effective for treating pustular and bacterial skin infections such as acne vulgaris.

Conveniently the immunosuppressive macrolide is selected from sirolimus, FK-506 or SDZ ASM 981. Sirolimus is a favoured alternative because it is also an effective antibiotic which is useful in the microbiological preservation of the formulation. The microbiological properties of sirolimus are also helpful in the treatment of scalp and flexural psoriasis, seborrhoeic dermatitis and in secondarily atopic eczema.

In preferred embodiments the permeation modulator may be an alkanoic or alkenic acid, preferably having 6 to 20 carbon atoms such as capric acid, octanoic acid, oleic acid or acids or such acids of intermediate chain length. The permeation modulator aids the penetration of the immunosuppressive macrolide or macrocyclic antibiotic through the stratum corneum, the principle barrier to the penetration of drugs. The stratum corneum is an aggregate of the stacked, flattened skeletons of keratin filled cells interspersed with lipid monolayer structures and water. The addition of the permeation modulator to the formulation results in the partial disruption of the barrier components, particularly the lipid structures. A gradient of the drug can then be produced across the stratum corneum particularly, which facilitates the diffusion of the immunosuppressive macrolide or macrocyclic lactone antibiotic across the stratum corneum into the living epidermis. The relative concentrations of the macrolide or antibiotic and the permeation modulator are chosen so that only partial penetration of the skin occurs; the macrocyclic lactone antibiotics or immunosuppressive macrolides reach the areas which require treatment but significant absorption of the said drugs into the systemic circulation is avoided thus reducing the likelihood of any systemic side effects.

Conveniently the permeation modulator is used in conjunction with a solvent system which includes an aromatic alcohol such as phenyl-alkanol or a biologically acceptable benzene derivative, with or without an admixture of monoglycerides and/or a fatty acid ester (e.g. isopropyl myristate). Other solvents. used, include benzaldehyde, benzyl benzoate and acetone. The combination of solvent and permeation modulator further optimises the passage of the immunosuppressive macrolide or the macrocyclic lactone antibiotic across the stratum corneum.

Preferably, the concentration of the macrocyclic lactone antibiotic or immunosuppressive macrolide is up to 10% by weight of the formulation. More preferably the concentration of the macrocyclic lactone antibiotic or immunosuppressive macrolide is either 0.5% to 5.9% or 6% to 12% by weight. Even more preferably the concentration of the macrocyclic antibiotic or immunosuppressive macrolide is either 1 to 5% or 6 to 8% by weight. A concentration of 0.05% to 2% is most preferable in the treatment of eczema. The term "% by weight" used herein refers to the "% by weight of the final formulation".

Preferably the above ranges of macrocyclic lactone antibiotic or immunosuppressive macrolide or analogue derivative or pro-drug thereof are used in an agent comprising a permeation modulator; wherein the concentration of the permeation modulator is 0.1% to 60% by weight. More preferably the concentration of the permeation modulator is either 0.1% to 39.9% or 40% to 80% by weight. Even more preferably the concentration of the permeation modulator is either 0.1% to 19.9%, 20% to 39.9% or 40% to 60%.

Preferably the above ranges of macrocyclic lactone antibiotic or immunosuppressive and permeation modulator are used in a formulation in conjunction with a solvent system; wherein the concentration of the solvent system is 5% to 90% by weight. More preferably the concentration of the solvent system is either 0.1% to 49.9% or 50% to 90% by weight. Even more preferably the concentration of the solvent system is either 0.1% to 19.9%, 20% to 39.9%, 40% to 69.9% or 70% to 90% by weight.

Preferably a thickening agent is present in the formulation. If the formulation is to be used topically, it should be of an appropriate consistency. Therefore, thickening agents such as cetostearyl alcohol or commercially available medical grade white soft paraffin may be added. These can reduce the penetration of the immunosuppressive agent but they are required for effective application. The formulations of the invention are particularly suitable for treatment of conditions of the scalp.

In addition to the liquid and solid vehicles set forth above, the formulations of the invention may additionally include one of the following: flavouring agents, lubricants, solubilizers, suspending agents, filler and glidants.

The formulation can also be dissolved or suspended in any pharmaceutically acceptable liquid carrier or vehicle such as water or a pharmaceutically acceptable oil or fat. Such a liquid carrier or vehicle can contain other pharmaceutically acceptable additives such as solubilizers, emulsifier, buffers, preservatives, suspending agents, thickening agents, colouring agents, viscosity regulators, stabilizers or osmo-regulators.

The invention will now be described, by way of illustration only, with reference to the following examples, tables and figures accompanying the specification FIG. 1 is a graphical representation of the effect on the flux ($\mu$g/hr/cm$^2$) of sirolimus (y) through the stratum corneum by varying the capric acid and benzyl alcohol ratio, where x is the percentage of capric acid in the benzyl alcohol.

FIG. 2 is a graphical representation of the effect on the flux ($\mu$g/hr/cm$^2$) of sirolimus (y) through the stratum corneum by varying the octanoic acid and benzyl alcohol ratio, where x is the percentage of octanoic acid in the benzyl alcohol.

FIG. 3 is a graphical representation of the effect on the flux ($\mu$g/hr/cm$^2$) of sirolimus (y) through the stratum corneum by varying the oleic acid and benzyl alcohol ratio, where x is the percentage of oleic acid in the benzyl alcohol.

FIG. 4 is a graphical representation of the effect on the flux ($\mu$g/hr/cm$^2$) of sirolimus (y) through the stratum corneum by varying the sirolimus concentration (mg/ml) (x) while keeping the capric acid to benzyl acid ratio constant.

FIG. 5 is a graphical representation of the results of the clinical score (y) determined after application of the sirolimus formulation ( ) and the control (:::) in Example 3.

FIG. 6 is a graphical representation of the difference in the clinical score after application with sirolimus formulation in Example 3, where y is the number of subjects in each group. A positive score (x) shows improvement with use of the active formulation.

FIGS. 1 to 4 were obtained by in vitro experimentation. The results were used to optimize the sirolimus concentration and the ratio of permeation enhancer and solvent used in in vivo experiments.

EXAMPLE 1

A formulation was formed of 8% sirolimus and 92% of a vehicle of capric acid (50%) with benzyl alcohol (50%). This was tested in single application experiments on four individuals with normal skin. Venous blood samples were taken at 4, 7 and 24 hours after application and no significant levels of sirolimus were detected using MSGCMS, which is able to detect sirolimus levels down to 0.1 ng/ml.

In parallel, skin biopsies were taken from the individuals after 7 hours, the biopsy samples were glued to a glass slide and serially sectioned horizontally into 4 layers each 0.7 mm thick and extracted with acetonitrile. The results are given in Table 1.

Table 1 shows the tissue concentrations of sirolimus 7 hours after application of capric acid: benzyl alcohol (50:50) containing sirolimus at 8%. The horizontal skin sections were each 0.7 mm. Accordingly, for example, the section of skin designated 2 was the horizontal layer of skin 0.7–1.4 mm from the surface of the skin.

| Section of skin | Sirolimus concentration μg/mg | | | |
|---|---|---|---|---|
| 1 = surface | A | B | C | D |
| 1 | 0.059 | 0.288 | 0.301 | 0.216 |
| 2 | Not done | 0.108 | 0.144 | 0.126 |
| 3 | 0.255 | 0.173 | 0.339 | 0.256 |
| 4 | 0.239 | 0.214 | 0.370 | 0.241 |

EXAMPLE 2

A formulation of sirolimus (2.2%) in a vehicle comprising isopropyl myristate 40%, benzyl alcohol 10% and capric acid 50% was tested in single application experiments on three individuals with normal skin. Venous blood samples were taken at 4, 7 and 24 hours after application and no significant levels of sirolimus were detected using MSGCMS. After 7 hours biopsy samples were taken from two of the individuals. These were bisected in parallel with the surface to give an upper and lower half, roughly corresponding to the epidermis and dermis. The skin was homogenised with acetonitrile and sirolimus concentration was determined by HPLC. The results are given in Table 2

Table 2 shows the tissue concentrations of sirolimus 7 hours after application of capric acid:isopropyl myristate-:benzyl alcohol (50:40:10) containing sirolimus at 2.2%.

| | Sirolimus Concentration μg/mg | |
|---|---|---|
| Level of skin segment | Subject A | Subject B |
| Upper (1) | 0 | 1.5 |
| Lower (2) | 0.333 | 0.5 |

EXAMPLE 3

A double blind, left-right comparison of the effect of applying topical sirolimus in formulations as described in Examples 1 and 2, to 24 patients with chronic (over three months) plaque psoriasis was conducted. (22 out of the 24 patients were eventually analysed.) A single target plaque was treated for the first 6 weeks with the lower potency formulation of Example 2. After this the active treatment was increased to the higher potency formulation of Example 1 for 6 weeks unless a clear improvement on one side had already occurred.

The study included adults with stable, clearly demarcated, chronic plaque psoriasis, and two, well matched, contralateral, comparable plaques about 50 cm² in area on opposite sides of the body. Subjects were all aged over 18 years, were able to apply creams and had no other significant medical problems. Transaminases were not more than twice the upper limit of normal and subjects were selected to avoid those likely to have a holiday in sunlight during the 6–12 weeks of the trial.

Before the trial started, there was a two week washout period in which only bland emollients were applied to the target lesions.

Treatment was randomised and double blind. Hands were thoroughly washed between the twice daily application of the test formulations. The active formulation was applied consistently to one plaque while a control comprising only the vehicle base was applied consistently to the plaque on the opposite side. Where possible the arms or elbows were selected as target areas as cross contamination is less likely at these sites.

Assessments were done at weeks 0, 2, 4 and 6 on the low potency treatment and at 8,10 and 12 on the higher dose formulation, provided there were no signs or laboratory evidence of toxicity. Clinical scoring was done at each attendance and areas traced at the start and finish of treatment. Biopsies from active and control lesions were performed at the end of treatment or at withdrawal. Biopsies were not done if an adverse event such as a reaction to the application occurred as this would influence the measures being assessed.

The lesions were also assessed at fortnightly intervals with subjective scoring on a scale of 0–8 for erythema, thickening, and scaling. Objective measures of improvement were performed on both lesions at the end of each treatment period (low and high formulations). These included pulsed A scan ultrasound measurement of lesion thickness and erythema measured with a reflectance erythema metre, both were averaged over 5 areas in each psoriatic lesion and were validated using a previous study which was performed using betamethasome as a reference.

At each visit we measured the full blood count, biochemistry, including urea, electrolytes, liver enzymes, bilirubin, calcium, magnesium, uric acid, glucose, amylase, muscle enzymes, lipids and cholesterol. Sirolimus levels were performed every 2 weeks during therapy. Samples for sirolimus levels were stored at minus 80° C. and shipped to a central reference laboratory for analysis by LC/MS/MS by Wyeth Ayerst Research.

In biopsies, epidermal thickness was measured and immunoperoxidase immunohistochemistry done using the following antibodies to count cells in a blinded fashion:

Thus, antibody Ki-67 was used to give a measure of hyperproliferation in the epidermis and CD4 helper lymphocytes were used to give a measure of auto-immune activity which drives psoriasis.

Cell counting in tissues was automated, using computer assisted image analysis (Seescan). Data was analysed by Student's T test for paired data and Wilcoxon's test.

Figure 5:
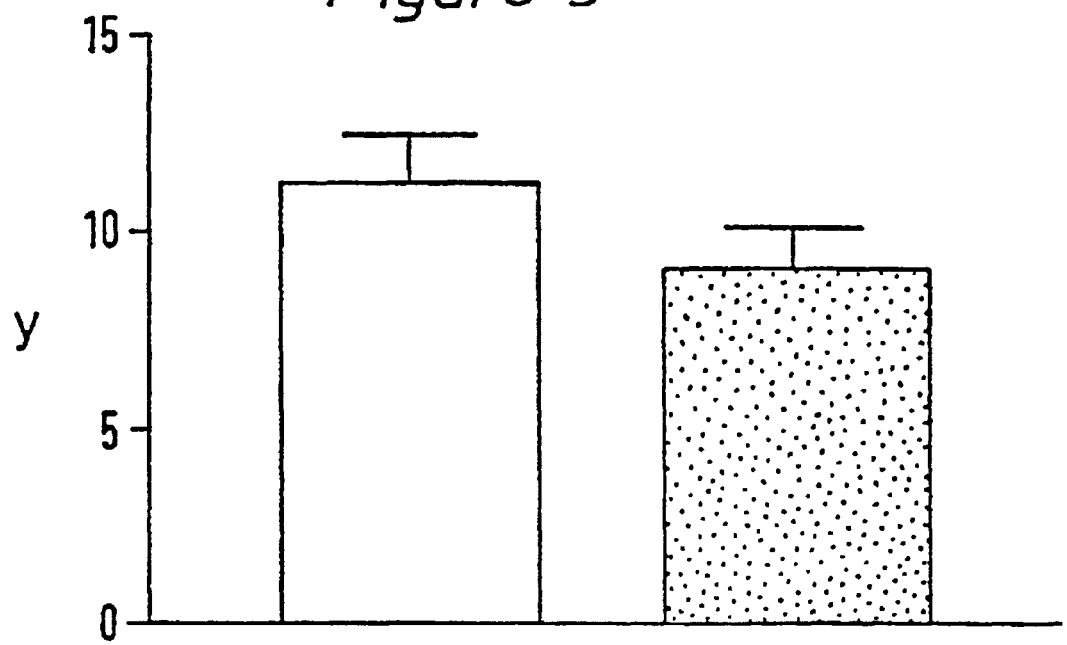
Figure 6:
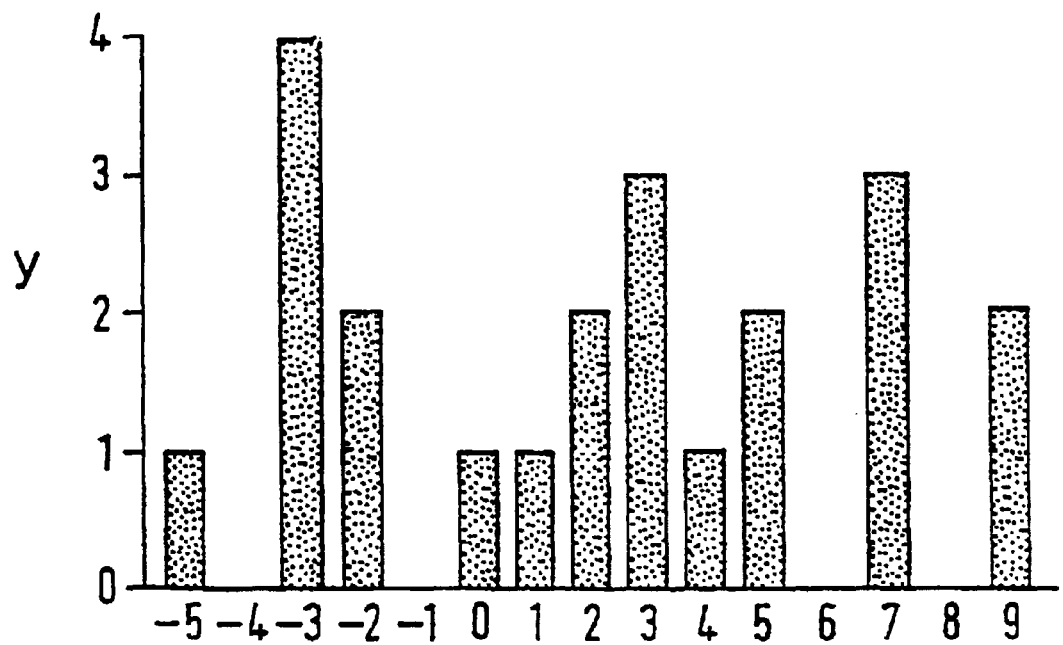

Comparison of the final scores, active vs placebo achieved significance at 0.032 by T test or Wilcoxon's test 0.0457, see Table 3 and FIGS. 5 and 6. The erythema measurements and ultrasound recordings were not significantly different. Three of the twenty-two patients developed contact sensitivity to the topical preparations one to benzyl alcohol, one to sirolimus and one to both of these.

The antibody tests with Ki-67 showed a significant reduction of proliferating cells from a mean of $83/mm^3$ in control to $55/mm^3$ with Sirolimus (rapamycin) to give a significance of P-0.027 (T test). Using CD4 cells control values were $61/mm^3$ against $32.7/mm^3$ means values following rapamycin to give a significance of P-0.0026 (T-test). The T-test were unpaired due to missing samples.

Table 3 shows the clinical response to topical sirolimus. The clinical score is measured on a scale of 0–24 with higher values indicating a better result, ultrasound thickness in mm and erythema measurement in arbitrary units.

|  | Sirolimus | | Control | | |
|---|---|---|---|---|---|
|  | Mean | S.D. | Mean | S.D. | Significance |
| Clinical Score | 11.2 | 5.8 | 9.1 | 4.8 | p = 0.032 |
| Ultrasound thickness | 2.99 | 0.6 | 2.96 | 0.72 | NS |
| Erythema measurement | 34.5 | 7.9 | 33.1 | 7.7 | NS |

These results show that penetration of sirolimus from a formulation described above does occur. It is thought that increased adsorption would occur through the scalp to effectively treat scalp psoriasis.

What is claimed is:

1. A topical formulation for the treatment of a dermatological condition which comprises a macrocyclic lactone antibiotic chosen from clarithromycin or an immunosuppressive macrolide chosen from sirolimus or SDZ ASM 981, and a permeation modulator which are present in relative amounts such that when a therapeutic amount is applied to the skin a minimal systemic effect is produced.

2. The formulation of claim 1 comprising up to 10% by weight of the macrocyclic lactone antibiotic or the immunosuppressive macrolide or analogue, derivative or pro-drug thereof and 1 to 60% by weight of the permeation modulator.

3. The formulation of claim 1 wherein the dermatological condition is psoriasis, alopecia, eczema dermatitis, lichen planus, lupus erthematosus, pyderma gangrenosum, vitiligo, graft versus host disease, pustular skin infections, bacterial skin infections or acne vulgaris.

4. The formulation of claim 3 wherein the dermatological condition is eczema dermatitis and the concentration of macrocyclic lactone antibiotic or immunosuppressive macrolide is 0.05% to 2% by weight.

5. The formulation of claim 1 further comprising a thickening agent.

6. The formulation of claim 5 wherein the thickening agent is white soft paraffin, cetostearyl alcohol, yellow soft paraffin, cetyl alcohol, steryl alcohol, divalent carboxylic acid soaps or camauber wax.

7. A method for the treatment of a dermatological condition comprising administering an effective amount of the topical formulation of claim 1.

8. A topical formulation for the treatment of a dermatological condition which comprises a macrocyclic tactone antibiotic chosen from azithromycin or clarithromycin or an immunosuppressive macrolide chosen from sirolimus, FK506 or SDZ ASM 981, and a permeation modulator which are present in relative amounts such that when a therapeutic amount is applied to the skin a minimal systemic effect is produced and wherein the permeation modulator is used in conjunction with a solvent system comprising an aromatic alcohol or a biologically acceptable benzene derivative, with or without an admixture of monoglycerides and a fatty acid ester.

9. The formulation of claim 8 wherein the solvent system comprises an aromatic alcohol or a biologically acceptable benzene derivative, with or without an admixture of a fatty acid ester.

10. The formulation of claim 8 wherein the permeation modulator comprises capric acid and the solvent system comprises benzyl alcohol.

11. The formulation of claim 8 wherein the concentration of the solvent system is 5% to 90% by weight.

12. The formulation of claim 8 further comprising a thickening agent.

13. The formulation of claim 12 wherein the thickening agent is white soft paraffin, cetostearyl alcohol, yellow soft paraffin, cetyl alcohol, steryl alcohol, divalent carboxylic acid soaps or camauber wax.

14. A method for the treatment of a dermatological condition comprising administering an effective amount of the topical formulation of claim 10.

15. The formulation of claim 8 comprising up to 10% by weight of the macrocyclic lactone antibiotic or the immunosuppressive macrolide or analogue, derivative or pro-drug thereof and 1 to 60% by weight of the permeation modulator.

16. The formulation of claim 8 wherein the permeation modulator is an alkanoic acid or alkenic acid.

17. The formulation of claim 16 wherein the alkanoic acid or alkenic acid is capric acid, octanoic acid or oleic acid.

18. The formulation of claim 8 wherein the dermatological condition is psoriasis, alopecia, eczema dermatitis, lichen planus, lupus erthematosus, pyderma gangrenosum, vitiligo, graft versus host disease, pustular skin infections, bacterial skin infections or acne vulgaris.

19. The formulation of claim 18 wherein the dermatological condition is eczema dermatitis and the concentration of macrocyclic lactone antibiotic or immunosuppressive macrolide is 0.05% to 2% by weight.

20. The formulation of claim 1 wherein the macrocyclic lactone antibiotic is clarithromycin.

21. The formulation of claim 1 wherein the macrocyclic lactone antibiotic is clarithromycin and wherein the permeation modulator is an alkanoic acid or alkenic acid.

22. The formulation of claim 21 wherein the alkanoic acid or alkenic acid is capric acid, octanoic acid or oleic acid.

23. The formulation of claim 1 wherein the immunosuppressive macrolide is sirolimus.

24. The formulation of claim 1 wherein the immunosuppressive macrolide is sirolimus and wherein the permeation modulator is an alkanoic acid or alkenic acid.

25. The formulation of claim 24 wherein the alkanoic acid or alkenic acid is capric acid, octanoic acid or oleic acid.

26. The formualtion of claim 1 wherein the immunosuppressive macrolide is SDZ ASM 981.

27. The formulation of claim 1 wherein the immunosuppressive macorlide is SDZ ASM 981 and wherein the permeation modulator is an alkanoic acid or alkenic acid.

28. The formulation of claim 27 wherein the alkanoic acid or alkenic acid is capric acid, octanoic acid or oleic acid.

* * * * *

UNITED STATES PATENT AND TRADEMARK OFFICE
CERTIFICATE OF CORRECTION

PATENT NO. : 6,958,153 B1
DATED : October 25, 2005
INVENTOR(S) : Anthony Ormerod et al.

It is certified that error appears in the above-identified patent and that said Letters Patent is hereby corrected as shown below:

Column 7,
Line 43, "camauber" should read -- carnauber --.
Line 48, "tactone" should read -- lactone --.

Column 8,
Line 15, "camauber" should read -- carnauber --.

Signed and Sealed this

Twentieth Day of December, 2005

JON W. DUDAS
*Director of the United States Patent and Trademark Office*